(12) United States Patent
Luloh et al.

(10) Patent No.: US 7,549,972 B2
(45) Date of Patent: Jun. 23, 2009

(54) TOOL FOR EXTRACTING VITREOUS SAMPLES FROM AN EYE

(75) Inventors: K. Peter Luloh, Stuart, FL (US); Frank H. J. Koch, Frankfurt A.M. (DE); Michael Annen, Fort Pierce, FL (US)

(73) Assignee: Insight Instruments, Inc., Stuart, FL (US)

( * ) Notice: Subject to any disclaimer, the term of this patent is extended or adjusted under 35 U.S.C. 154(b) by 247 days.

(21) Appl. No.: 11/463,465

(22) Filed: Aug. 9, 2006

(65) Prior Publication Data

US 2007/0078359 A1 Apr. 5, 2007

Related U.S. Application Data

(60) Provisional application No. 60/707,100, filed on Aug. 10, 2005.

(51) Int. Cl.
*A61B 17/20* (2006.01)
(52) U.S. Cl. .................................................... 604/22
(58) Field of Classification Search ................. 606/107, 606/166, 171, 170, 180; 604/22
See application file for complete search history.

(56) References Cited

U.S. PATENT DOCUMENTS

| 4,108,182 A * | 8/1978 | Hartman et al. ............. 606/171 |
| 4,368,734 A | 1/1983 | Banko |
| 4,475,904 A | 10/1984 | Wang |
| 4,674,502 A | 6/1987 | Imonti |
| 4,696,298 A | 9/1987 | Higgins et al. |
| 4,729,763 A | 3/1988 | Henrie |
| 5,047,008 A | 9/1991 | de Juan, Jr. et al. |
| 5,106,364 A | 4/1992 | Hayafuji et al. |
| 5,716,363 A | 2/1998 | Josephberg |
| 5,843,111 A | 12/1998 | Vijfvinkel |
| 5,893,862 A * | 4/1999 | Pratt et al. .................. 606/170 |
| 5,989,262 A | 11/1999 | Josephberg |
| 6,059,792 A | 5/2000 | Josephberg |

\* cited by examiner

*Primary Examiner*—Manuel A Mendez
(74) *Attorney, Agent, or Firm*—James H. Beusse; Beusse Wolter Sanks Mora & Maire, P.A.

(57) ABSTRACT

A unitary mechanical injector-vitrector hand tool for use in extracting vitreous material from an eye and injecting another fluid into the eye includes a housing body having a proximal end, a distal end and a variable volume cavity in the housing body for establishing a negative pressure or suction. A needle having a sharpened point and a central bore is connected to the proximal end of the housing body. An aperture is formed in a sidewall of the needle near the sharpened end. An inner hollow reciprocal cutter is fitted in the central bore of the needle and has a cutting edge adapted for travel across the aperture. A first manually actuatable lever is pivotably mounted to the housing body and coupled in driving relationship with the reciprocal cutter. A valve assembly is operatively positioned between the needle and the variable volume cavity and arranged to open to apply suction to the needle central bore as the reciprocal cutter travels across the aperture so as to withdraw vitreous material falling into the hollow cutter. A pressurized source of fluid is coupled by a conduit through the central bore of the needle and cutter and selectively actuated to replace the removed vitreous material with other material such as an antibiotic.

15 Claims, 3 Drawing Sheets

TOOL FOR EXTRACTING VITREOUS SAMPLES FROM AN EYE

SPECIFIC DATA RELATED TO THE INVENTION

This application claims the benefit of U.S. provisional application No. 60/707,100 filed Aug. 10, 2005.

The present invention relates to a form of vitrectomy tool and, more particularly, to a combinational tool that can be used for extracting samples of vitreous from an eyeball and replacing the extracted material with a drug or other substance.

BACKGROUND OF THE INVENTION

It is common practice to extract small amounts of vitreous material from a person's eye in order to provide a sample of the material for examination or in order to remove material so that antibiotics or other drugs may be injected into the eye. Typically, any injection into the eye can result in excess pressure being generated and cause damage to the eye. Accordingly, it is desirable that a volume of vitreous material be removed from the eye prior to injecting an equal volume of drugs into the eyeball.

Various instruments have been developed for this purpose, most of which have been relatively complicated requiring large amounts of supporting equipment. U.S. Pat. No. 6,059,792 describes a sutureless vitrectomy tool that can be used to perform a vitrectomy procedure including removing all of the vitreous material from an eye. However, this device requires an operating room environment and electrical connections to a hand held instrument that utilizes a linear motor to repetitively drive a cutting tool within a 23 gauge stainless steel needle for removing vitreous from the eye. U.S. Pat. Nos. 5,989,262 and 5,716,363 describe sutureless pars plana vitrectomy tools using electrically powered actuators.

SUMMARY OF THE INVENTION

The present invention comprises a unitary mechanical combination injector and vitrector in the form of a manually operable hand tool that can be used when it is only necessary to remove a small volume of vitreous material from the eye ("vitrectomy") in order to provide room for injection of antibiotics or other drugs into the eye. For example, the hand tool may be used to inject an antibiotic into a patient's eye by first removing sufficient vitreous material to approximate the volume of antibiotic fluid so as to prevent an undesirable increase in intraocular pressure. Using the hand tool of the present invention, a drug may be injected into a patient's eyeball in a procedure that may be performed in a doctor's office rather than having to be in a sterile environment of an operating room. Further, the present invention may be designed as a disposable item that is used once and then discarded, thus preventing cross-contamination from multiple use between different patients.

BRIEF DESCRIPTION OF THE DRAWINGS

FIG. 1A is an enlarged sectional view of a portion of the device of FIG. 1;

DETAILED DESCRIPTION OF THE INVENTION

Figure 1:
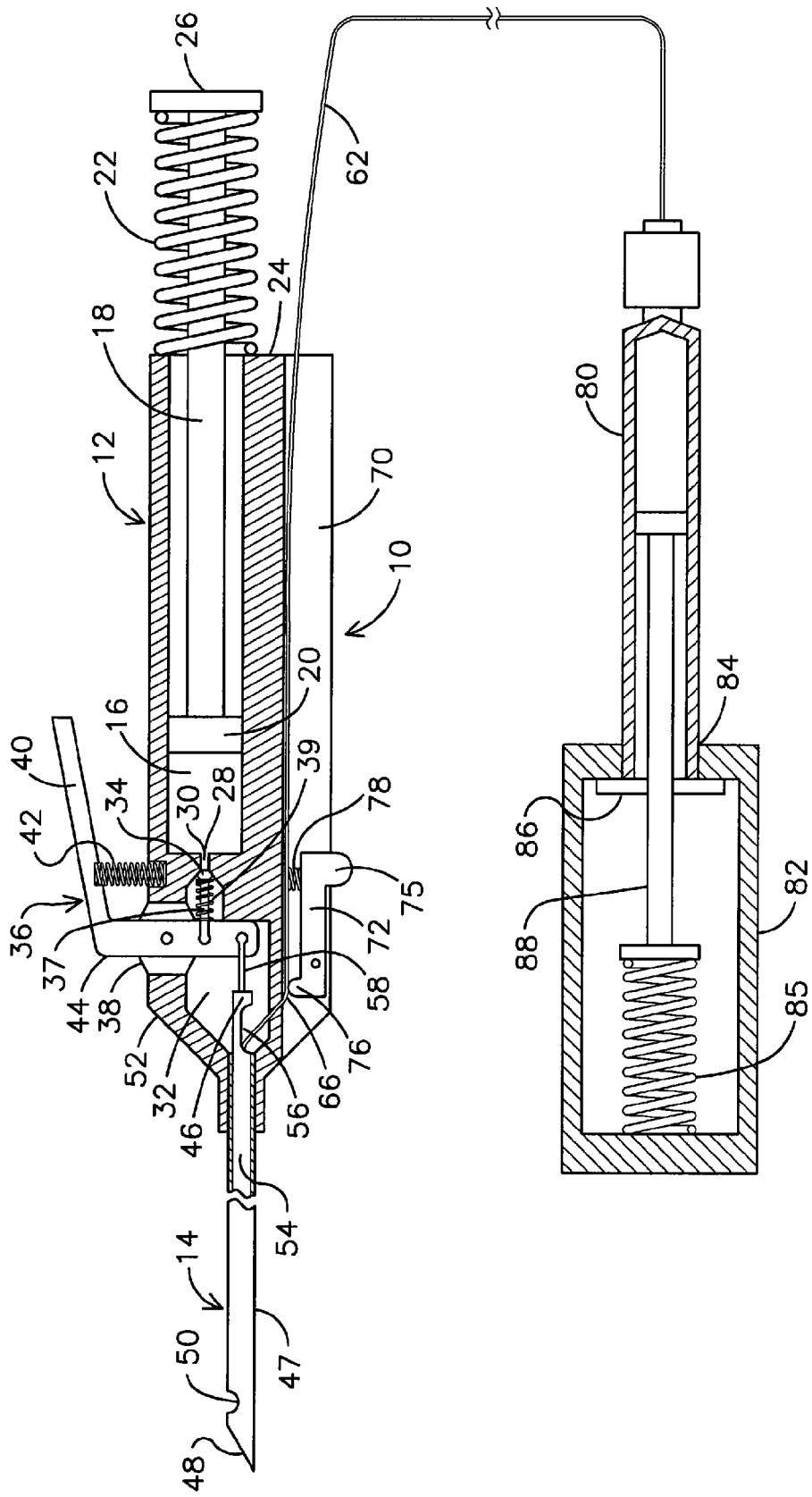
FIG. 1 is a cross-sectional drawing taken along a longitudinal axis of one form of the present inventive injector-vitrector device.

Referring to the drawings in general and in particular to FIG. 1 and the enlarged section of FIG. 1 shown in FIG. 1A, there is shown one embodiment of the present invention in a form of a manually operated hand tool 10. The tool 10 includes a housing body or body portion 12 and a needle portion 14. The body portion 12 includes several cavities, the largest of which is a vacuum, i.e., a negative pressure, or aspiration cavity 16. A plunger 18 is situated in the cavity 16 and includes a plunger end 20 that sealingly engages the inner surfaces of the body 12 defining the cavity 16. The plunger end 20 may be an elastomeric material or provided with an elastomeric seal such as an O-ring. A spring 22 is positioned about the plunger and reacts between an end 24 of the housing 12 and a cap 26 on the plunger.

At the inner end 28 of cavity 16 there is an orifice 30 that provides an opening into a second cavity 32. The orifice 30 is sealed by a plug 34 attached to a lever 36 via an elongate arm 37 that is held in an extended position by a spring 39. The arm 37 is captured at end 41 in a slot 43 formed in lever 36. The lever 36 is seated in a ball pivot 38 that allows the lever to be pivoted without disrupting the integrity of the cavity 32. The lever 36 has an outer arm 40 that is held in the position shown in FIG. 1 by the action of a spring 42. The spring 42 reacts between the body 12 and an underside of the arm portion 40 to pivot the lever 36 in a direction to maintain the plug 34 seated in the orifice 30. Spring 42 is seated in aperture 45 formed in body 12.

The lever 36 is essentially an L-shaped member in which the outer arm portion 40 is arranged at an obtuse angle with respect to the other arm portion 44. The plug 34 is attached to the arm portion 44 via arm 37. When the arm portion 40 is pressed down causing the lever 36 to pivot, the arm portion 44 moves in a clockwise direction thereby pulling the plug 34 out of the orifice 30 allowing transfer of material between cavity 32 and cavity 16.

Also coupled to the arm portion 44 via connecting rod 58 is a second elongated member 46 (an inner cutter) that extends from an end of the arm portion 44 outward through a central bore of the needle portion 14. The needle portion 14 includes an outer needle 47 and the inner cutter 46. The needle 47, in addition to having a sharpened end 48 to facilitate insertion into the eye, is also provided with an aperture or cut out 50 into which vitreous material will flow when the needle portion 14 is inserted into an eye. As can be seen in FIGS. 1 and 1A, the housing body 12 includes an end portion 52 that engages and holds the outer needle 47 in fixed relationship to the body 12. It can also be seen that the elongated member 46 comprises a hollow tube that fits within the needle 47 and also has a side opening 56 within housing body 12. The connecting rod 58 connects the hollow tube member 46 to the arm portion 44. Accordingly, when the lever 36 is pressed downward, not only does the plug 34 retract from the orifice 30 but also the tube member 46 is driven forward through the needle 47 so that the distal edge 60 of the tube member 46 severs any material protruding into the opening or aperture 50. The action of the inner tube within the needle is more clearly shown in FIGS. 2A and 2B.

Figure 2:
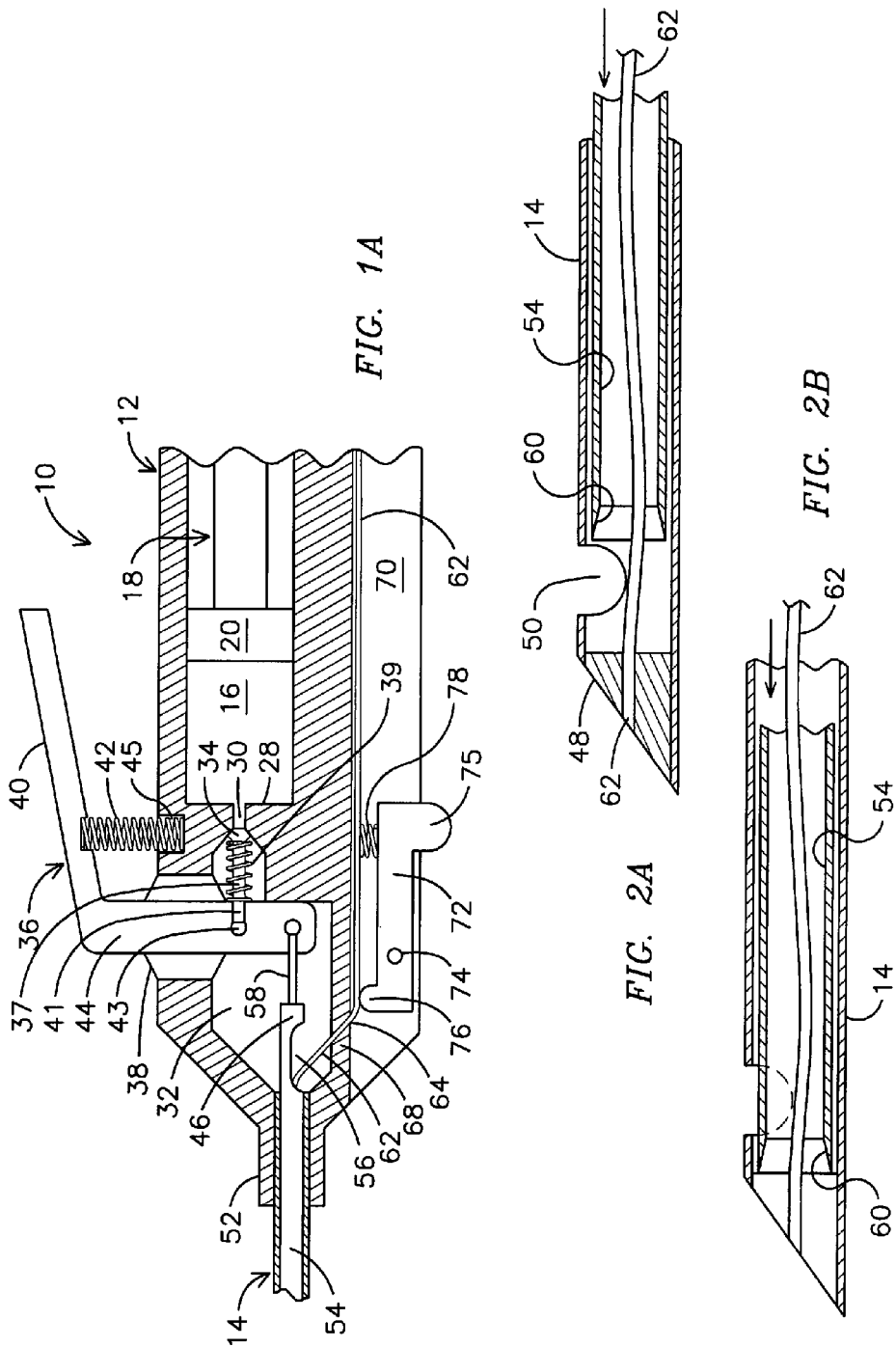
FIGS. 2A and 2B are cross-sectional views of the needle portion of the device of FIG. 1 showing two positions of the inner cutter.

FIGS. 2A and 2B show an enlargement of the needle portion 14 of FIG. 1. It can be seen that the inner tube 46 fits snugly within the inner opening through needle 47. The end of the tube 46 is formed with a sharpened edge at 60 so that when the inner cutting tube member 46 is pressed forward past the aperture 50, member 46 acts as a reciprocal cutter with the sharpened edge cutting off any material protruding into the aperture 50 and causing the cut material to drop into the cavity formed within the inner tube member 46. FIG. 2B illustrates the position of the inner tube member 46 as it has been urged forward past the aperture 50. In FIGS. 2A and 2B, it will also be seen that there is another smaller diameter tube 62 extending through the inner tube 54 and out to the end of the needle portion 14. The tube 62 is used to transport liquid such as antibiotics or drugs or even water into the eye to replace the vitreous material that is removed by the cutting action of the needle and inner tube 54. While the needle portion 14 has been described in what is believed to be a preferred embodiment, it will be recognized that other forms of cutters may be used in the invention. See, for example, cutter descriptions in U.S. Pat. No. 5,716,363. The only requirement is to be able to puncture the eye to excise a portion of the vitreous material and introduce that material into a tube through which it can be removed from the eye by suction. Accordingly, the term "needle portion" is intended to include all such cutters having this capability.

Turning back to FIG. 1, the inner tube 62 exits the tube 54 through the opening 56 and then passes through another opening at 64 in wall 68 of cavity 32. The opening 64 and tube 62 are sized to create a generally leak free connection through the wall 68. The tube 62 then proceeds through a longitudinal opening 70 and extends out the rear end of the body 12. The path of the tube 62 is guided through the passage 70 so that it passes under a second lever 72. The lever 72 has a pivot point at 74 and an inwardly extending arm or protrusion 76 positioned to engage the tube 62. The lever arm 76 is held in contact with the tube 62 by means of a spring 78 pushing on the lever 72 so as to cause a clockwise-directed force on the lever. The spring 78 and lever 72 are sized and arranged so that there is sufficient force exerted on tube 62 to collapse the tube and prevent fluid flow therethrough. The pressure on the tube 62 can be released by pressing downward on lever arm 75 against action of the spring 78 to cause the lever to pivot sufficiently to release enough pressure on the tube so that a flow of fluid can be forced through the tube.

The tube 62 extends outward from the hand tool 10 and connects to a mechanical pressurization system comprising a conventional syringe 80 and a spring-loaded mechanism 82. The syringe 80 is typically supplied with a needle tip (not shown) that is then inserted into a drug container in a conventional manner and a measured amount of drug is drawn into the syringe. In this application, the needle is then removed from the end of the syringe and the tube 62 connected to the syringe in its place. The syringe is then coupled to the spring actuator 82 by simply depressing the spring and inserting the upper part of the syringe into the slot 84 so that the top end 86 of the syringe rests on an inner surface around the slot 84. The spring is then released to press against the plunger 88 of the syringe. The spring 90 pressing against the plunger 18 maintains a fixed pressure of fluid in the tubing 62. As would be recognized, the syringe would be actuated initially to force fluid from the syringe through the tubing 62 until some amount of fluid is released at the end of the tubing at the sharpened end 48 of the needle 14. The lever 72 would then be released to clamp the tubing before inserting the needle 14 into an eye of a patient.

The system of FIG. 1 requires that the plunger 18 be depressed into the cavity 16 before inserting the needle 14 into an eye. Pressing the plunger downward will cause the plug 34 to open slightly at orifice 30 so that the air will be expelled out of the needle 14. However, the sealing action of the plug 34 will prevent air from leaking from the cavity 32 back into the cavity 16. Once the needle 14 is inserted into an eye, the lever arm 40 can be repetitively depressed and released to cause the inner tube 54 to move cyclically within the needle 14 to thereby cut off portions of the vitreous that flow into the aperture 50. At the same time that the lever arm 40 is depressed to actuate the cutting action of the tube 54, the plug 34 is released from the orifice 30 so that a vacuum pressure is created by the action of the plunger 18 being urged out of the cavity 16 by spring 22. This action draws the small pieces of vitreous into the tube 54 where they will be eventually drawn into the cavity 32. When the physician has removed a sufficient quantity of the vitreous material, he can depress the lever 72 to allow the fluid from syringe 80 to flow through the tube 62 and into the opening formed within the eye by removal of the vitreous material. Typically, the physician is using visual observation to determine when a sufficient volume of vitreous material has been removed and also to determine when a sufficient quantity of fluid has been inserted to replace the vitreous material. However, the syringe 80 is also calibrated so that a measured quantity of drug or other fluid may be injected into the eye in the region in which the vitreous material has been removed.

Figure 3:
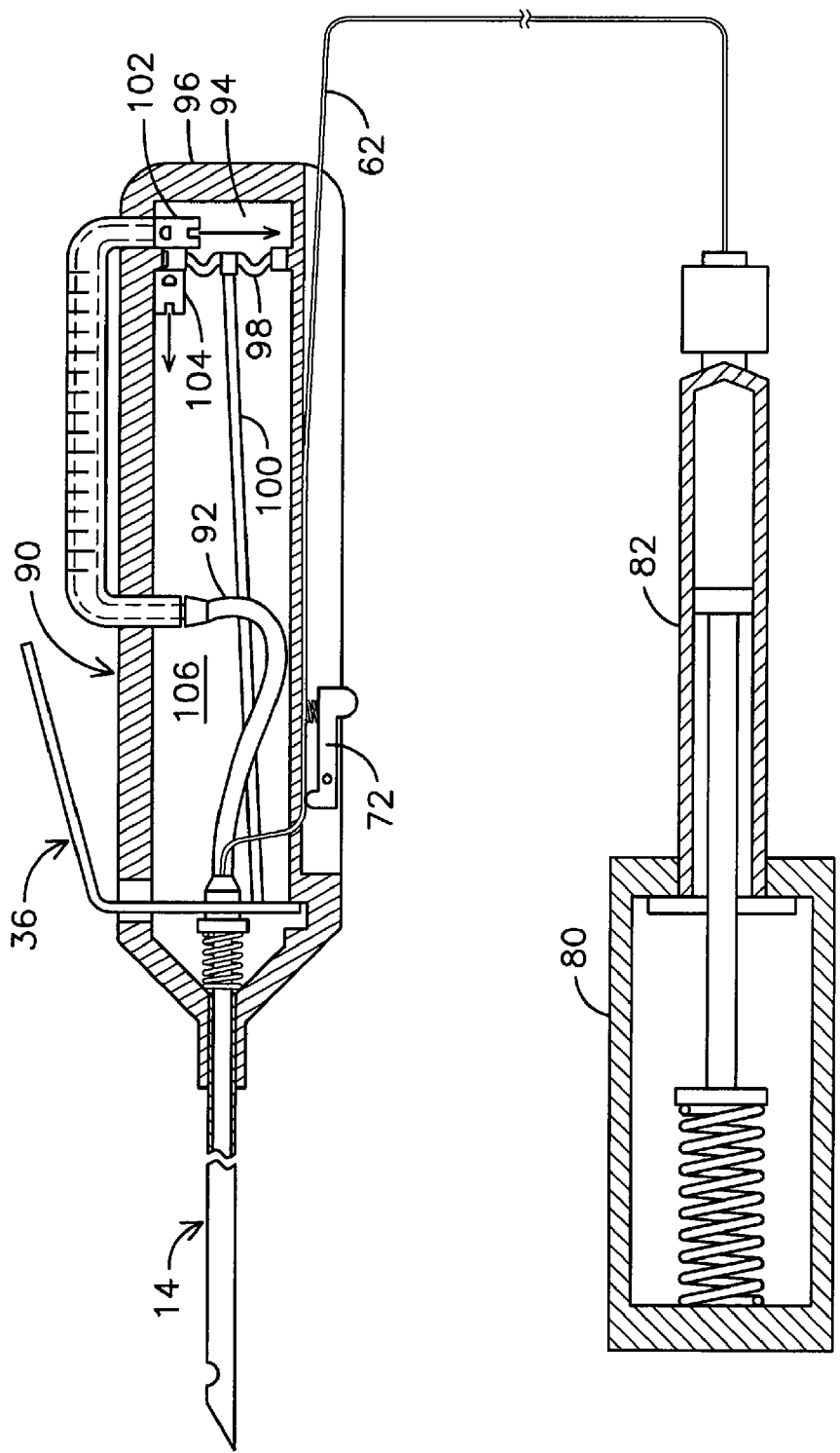
FIG. 3 is a cross-sectional drawing of another embodiment of the inventive injector-vitrector device.

FIG. 3 illustrates another embodiment of the present invention in which the suction action to remove vitreous fluid from the eye is obtained by mechanically cycling a membrane. Here, the needle portion 14 structure remains the same as in FIG. 1 but the main body portion is modified to create a closed housing 90. The pair of levers 36 and 72 are each mounted to the housing 90 similar to the structure of FIG. 1 and the tube 62 still connects to the external source of fluid at syringe 80 and the spring loaded mechanism 82. However, the tube 62 now passes into a suction tube 92 within housing 90. The suction tube 92 is connected at one end to the needle 14 so as to be able to create a vacuum or suction action within the needle. Another end of the tube 92 is connected to a secondary cavity 94 located within the housing 90. The cavity 94 is formed between a back end 96 of housing 90 and a flexible membrane 98.

A connecting rod 100 extends through housing 90 and connects at one end to about a center point of membrane 98. An opposite end of rod 100 is coupled to lever 36 such that pressing and releasing of lever arm 40 causes a reciprocating motion of rod 100 resulting in movement of membrane 98. As membrane 98 is pulled away from end wall 96, the fluid volume defined within the cavity 94 is increased. A one-way valve 102 allows fluid, air or liquid, to be drawn into cavity 94 via tube 92 as the membrane is pulled forward. When the lever 36 is released, the membrane moves toward rear wall 96 thereby decreasing the volume of cavity 94. A second one-way valve 104 provides a path for fluid to exit cavity 94 and be pushed into the large cavity 106 defined within housing 90. While the tube 92 is shown exiting the cavity 106 before being coupled to the cavity 94, it will be appreciated that different connections could be made to achieve the same result.

It will be appreciated that the present invention provides an advantageous way of removing small samples of vitreous material from an eye in order to provide space in the eye for injection of antibiotics or other drugs. Further, the device described herein can be constructed as a disposable device and provided as a pre-package sterile system. Still further, the device does not require any electrical connections and therefore simplifies the use such that it could be employed in non-operating room environment.

What is claimed is:

1. A unitary mechanical injector-vitrector hand tool comprising:

a housing body having a proximal end and a distal end;

a variable volume cavity in the housing body for establishing a negative pressure;

a needle connected to the proximal end of the housing body, the needle having a central bore extending therethrough and an aperture extending into the central bore from a radially outer surface;

an inner reciprocal cutter fitted in the central bore of the needle and having a cutting edge adapted for travel across the aperture;

a first manually actuatable lever pivotably mounted to the housing body and coupled in driving relationship with the reciprocal cutter; and a valve assembly operatively positioned between the needle and the variable volume cavity and arranged to open to apply the negative pressure to the needle central bore when the reciprocal cutter travels across the aperture.

2. The hand tool of claim 1 and including a pressurized source of fluid and a conduit coupling the source of fluid through the central bore of the needle.

3. The hand tool of claim 2 and including a second manually operable lever pivotally mounted to the housing body and operably associated with the conduit for controlling the flow of fluid through the conduit.

4. The hand tool of claim 3 wherein the second manually operable lever includes a protrusion for engaging the conduit and a spring for urging the protrusion into engagement with the conduit, the conduit being flexible so as to be crimped by engagement with the protrusion to prevent the flow of fluid therethrough.

5. The hand tool of claim 1 wherein the variable volume cavity comprises a tubular opening extending from the distal end of the housing body and a spring loaded plunger seated in the opening, the plunger being urged in a direction to increase the volume of the cavity so as to create the negative pressure therein.

6. The hand tool of claim 1 wherein the variable volume cavity comprises a closed cavity formed between an end wall at the distal end of the housing body and a flexible membrane attached within the housing body spaced from the end wall, the flexible membrane being coupled to the first lever so as to be moved to increase the volume of the variable volume cavity when the lever actuates the reciprocal cutter to create a negative pressure therein.

7. The hand tool of claim 6 and including a flexible tube coupling the closed cavity to the central bore of the needle.

8. The hand tool of claim 7 and including a pair of one-way valves operatively associated with the closed cavity, one of the one-way valves being coupled in fluid flow relationship with the flexible tube so as to allow flow from the tube into the closed cavity, another of the one-way valves being coupled in fluid flow relationship with the closed cavity so as to allow fluid flow out of the closed cavity when the cavity volume is decreased.

9. A sutureless intraocular manually operable surgical tool for removing material from an eye of a patient and replacing removed material with other fluid comprising;

(a) a housing body having a proximal end and a distal end;

(b) a hollow needle coupled to said proximal end of said housing, wherein said needle is of a size sufficient to fit through an opening in the eye small enough to heal without sutures, said needle having a sidewall defining a longitudinal bore, said sidewall being provided with an aperture;

(c) an inner cutter having a cutting edge telescopically received in said longitudinal bore of said needle and adapted for travel of said cutting edge across said aperture;

(d) a pivoting lever having a first arm extending outward of the housing body and a second arm extending into the housing body, said second arm being drivingly coupled to said inner cutter for effecting reciprocating motion of said inner cutter upon manual movement of said first arm;

(f) a suction tube provided in operable communication with said longitudinal bore;

(g) an injection tube provided in operable communication with said longitudinal bore; and (h) valve means operably couple to each of said suction tube and said injection tube to control the application of suction to said longitudinal bore and the injection of fluid into said longitudinal bore.

10. The surgical tool of claim 9 further comprising a pressurized source of fluid coupled to the injection tube.

11. The surgical tool of claim 10 further comprising a second manually operable lever pivotally mounted to the housing body and operably associated with the injection tube for controlling the flow of fluid through the injection tube.

12. The surgical tool of claim 11 wherein the second manually operable lever includes a protrusion for engaging the injection tube and a spring for urging the protrusion into engagement with the injection tube, the injection tube being flexible so as to be crimped by engagement with the protrusion to prevent the flow of fluid therethrough.

13. The surgical tool of claim 9 comprising a first variable volume cavity formed between an end wall at the distal end of the housing body and a flexible membrane attached within the housing body spaced from the end wall, the flexible membrane being coupled to the pivoting lever so as to be moved to increase the volume of the variable volume cavity when the lever actuates the reciprocal cutter to create a negative pressure therein.

14. The surgical tool of claim 13 wherein the suction tube is coupled between the variable volume cavity and the central bore of the needle.

15. The surgical tool of claim 13 and including a pair of one-way valves operatively associated with the variable volume cavity, one of the one-way valves being coupled in fluid flow relationship with the suction tube so as to allow flow from the suction tube into the variable volume cavity, another of the one-way valves being coupled in fluid flow relationship with a second cavity so as to allow fluid flow out of the variable volume cavity when the cavity volume is decreased.

* * * * *